US012702293B2

(12) United States Patent
Carlsson et al.

(10) Patent No.: US 12,702,293 B2
(45) Date of Patent: Aug. 11, 2026

(54) IMPLICIT GAZE AND FOCUS DISTANCE CALIBRATION

(71) Applicant: Distance Technologies Oy, Helsinki (FI)

(72) Inventors: Thomas Carlsson, Vantaa (FI); Mikko Strandborg, Hangonkylä (FI)

(73) Assignee: Distance Technologies Oy, Helsinki (FI)

( * ) Notice: Subject to any disclaimer, the term of this patent is extended or adjusted under 35 U.S.C. 154(b) by 264 days.

(21) Appl. No.: 18/735,608

(22) Filed: Jun. 6, 2024

(65) Prior Publication Data

US 2025/0375108 A1 Dec. 11, 2025

(51) Int. Cl.

| | |
|---|---|
| ***A61B 3/11*** | (2006.01) |
| ***G02B 27/00*** | (2006.01) |
| ***G06T 7/55*** | (2017.01) |
| ***G06V 40/18*** | (2022.01) |

(52) U.S. Cl.

CPC .......... *A61B 3/111* (2013.01); *G02B 27/0093* (2013.01); *G06T 7/55* (2017.01); *G06V 40/18* (2022.01)

(58) Field of Classification Search

CPC ................ A61B 3/111; G02B 27/0093; G02B 2027/0138; G06T 7/55; G06V 40/18; G06V 20/597; B60K 35/233; G06F 3/0304; G06F 3/013

USPC .......................................................... 351/204

See application file for complete search history.

(56) References Cited

U.S. PATENT DOCUMENTS

| | | | | |
|---|---|---|---|---|
| 10,996,746 | B2 * | 5/2021 | Ortiz Egea | G02B 27/0093 |
| 11,568,560 | B2 * | 1/2023 | Fogelström | G06V 20/597 |
| 2015/0085251 | A1 * | 3/2015 | Larsen | G06F 3/013 351/206 |
| 2015/0160726 | A1 * | 6/2015 | Sullivan | G02B 27/0093 345/156 |
| 2016/0139665 | A1 | 5/2016 | Lopez et al. | |
| 2017/0236304 | A1 | 8/2017 | Kempinski et al. | |
| 2020/0027245 | A1 * | 1/2020 | Arkhipau | G06F 18/214 |
| 2020/0121183 | A1 * | 4/2020 | Ortiz Egea | G02B 27/0093 |
| 2021/0026445 | A1 | 1/2021 | Stoner | |

(Continued)

OTHER PUBLICATIONS

European Patent Office, Extended European Search Report, Application No. 25177297.6, Mailed Jul. 16, 2025, 5 pages.

*Primary Examiner* — William R Alexander

(74) *Attorney, Agent, or Firm* — Ziegler IP Law Group, LLC.

(57) ABSTRACT

Images of a user's face are captured at a plurality of time instants. Tracking parameters are determined, tracking parameters include: a pose of the user's head, positions of eyeballs, and at least one of: relative positions of irises with respect to boundaries of the eyeballs, relative positions of irises with respect to corners, shapes of the user's eyes. Uncalibrated gaze vectors of the user's eyes are estimated. A set of uncalibrated gaze vectors is generated. The uncalibrated gaze vectors of the set are stored along with corresponding time instants and tracking parameters. A first subset of uncalibrated gaze vectors whose direction matches with a predefined forward axis of vision, is selected. For the uncalibrated gaze vectors, corresponding tracking parameters are fetched. A maximum distance between the irises is determined. The maximum distance is considered as an interpupillary distance.

18 Claims, 4 Drawing Sheets

(56) References Cited

U.S. PATENT DOCUMENTS

| | | | | |
|---|---|---|---|---|
| 2021/0350565 | A1* | 11/2021 | Fogelström | G06T 7/251 |
| 2024/0103679 | A1* | 3/2024 | McKenzie | G06T 19/006 |
| 2024/0104860 | A1* | 3/2024 | McKenzie | G02B 27/0172 |
| 2024/0104861 | A1* | 3/2024 | DeDonato | G06F 3/012 |
| 2024/0152244 | A1* | 5/2024 | DeDonato | G06F 1/163 |

* cited by examiner

IMPLICIT GAZE AND FOCUS DISTANCE CALIBRATION

TECHNICAL FIELD

The present disclosure relates to systems incorporating implicit gaze and focus distance calibrations. The present disclosure also relates to methods incorporating implicit gaze and focus distance calibrations.

BACKGROUND

Head-up display (HUD) technology has emerged as a significant advancement across various domains (for example, automotive sectors, aviation sectors, military sectors, and the like) for presenting visual information to users without diverting their attention from their primary tasks, for example, such as driving a vehicle. Some HUDs utilise a head-pose tracking system to determine a viewing direction from where the visual information is to be displayed to user(s).

However, ensuring an accurate operation of the HUD relies heavily on a gaze-tracking quality and estimation of focal depths in non-invasive remote systems. There are several challenges in accurately estimating an optical axis of a human eye and in achieving precise gaze and focal depth estimation in such non-invasive remote systems. Firstly, the human eye has a distinct optical axis, which may deviate from its physical axis. Consequently, accurately estimating the optical axis with an error margin below 1 degree is extremely challenging without employing a calibration method. Secondly, gaze estimation and focal depth estimation in the non-invasive remote systems face inherent inaccuracies, for example, due to limitations in head pose estimation, constraints associated with fixed cornea reflectors (namely, glint-based eye tracking), and a reduction in a reduction of image resolution. Thirdly, achieving accurate gaze estimation necessitates an explicit gaze calibration process to be undergone by users before each session of displaying the visual information. However, this is highly inconvenient and cumbersome from a user experience (UX) standpoint, and thus an overall viewing experience of the user is adversely affected, and becomes unrealistic and non-immersive. Moreover, in some existing systems, pre-recorded calibration databases are utilised for generating a basic generic calibration model that is likely unreliable and not suitable for different users.

Therefore, in light of the foregoing discussion, there exists a need to overcome the aforementioned drawbacks.

SUMMARY

The present disclosure seeks to provide a system and a method which facilitate a simple, yet accurate, reliable, and implicit way to calibrate uncalibrated gaze vectors and a focusing distance of user's eyes, which eliminates a need for the user to perform explicit calibration tasks, unlike in the case of prior art. The aim of the present disclosure is achieved by a system and a method which incorporate implicit gaze and focus distance calibration, as defined in the appended independent claims to which reference is made to. Advantageous features are set out in the appended dependent claims.

Throughout the description and claims of this specification, the words "comprise", "include", "have", and "contain" and variations of these words, for example "comprising" and "comprises", mean "including but not limited to", and do not exclude other components, items, integers or steps not explicitly disclosed also to be present. Moreover, the singular encompasses the plural unless the context otherwise requires. In particular, where the indefinite article is used, the specification is to be understood as contemplating plurality as well as singularity, unless the context requires otherwise.

BRIEF DESCRIPTION OF THE DRAWINGS

FIG. 4A illustrates an enclosed space where a system incorporating implicit gaze and focus distance calibration is employed, while FIG. 4B illustrates uncalibrated gaze vectors of user's eyes, while

DETAILED DESCRIPTION OF EMBODIMENTS

Figure 1:
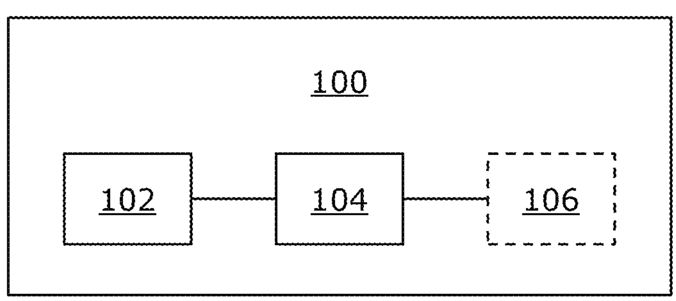
FIG. 1 illustrates a block diagram of an architecture of a system incorporating implicit gaze and focus distance calibration, in accordance with an embodiment of the present disclosure.

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In a first aspect, an embodiment of the present disclosure provides a system comprising:

- at least one tracking camera; and
- at least one processor configured to:
  - capture a plurality of images of a user's face at a plurality of time instants, using the at least one tracking camera;
  - process a given image captured at a given time instant, to determine a plurality of tracking parameters comprising: a pose of the user's head, positions of eyeballs of the user's eyes, and at least one of: relative positions of irises of the user's eyes with respect to boundaries of the eyeballs, relative positions of irises of the user's eyes with respect to corners of the user's eyes, shapes of the user's eyes;
  - estimate uncalibrated gaze vectors of the user's eyes corresponding to the given time instant, based on the plurality of tracking parameters determined from the given image;
  - generate a set of uncalibrated gaze vectors of the user's eyes corresponding to the plurality of time instants, by performing said processing and said estimation for each of the plurality of images;
  - store at least temporarily the uncalibrated gaze vectors of the set along with corresponding time instants and corresponding pluralities of tracking parameters;

select, from amongst the set of uncalibrated gaze vectors, a first subset of uncalibrated gaze vectors whose direction matches with a predefined forward axis of vision;

for the uncalibrated gaze vectors of the first subset, fetch corresponding pluralities of tracking parameters;

determine a maximum distance between the irises of the user's eyes, based on the corresponding pluralities of tracking parameters fetched for the uncalibrated gaze vectors of the first subset; and consider the maximum distance as an interpupillary distance of the user for focusing distances greater than a predefined threshold distance.

In a second aspect, an embodiment of the present disclosure provides a method comprising:

capturing a plurality of images of a user's face at a plurality of time instants, using at least one tracking camera;

processing a given image captured at a given time instant, to determine a plurality of tracking parameters comprising: a pose of the user's head, positions of eyeballs of the user's eyes, and at least one of: relative positions of irises of the user's eyes with respect to boundaries of the eyeballs, relative positions of irises of the user's eyes with respect to corners of the user's eyes, shapes of the user's eyes;

estimating uncalibrated gaze vectors of the user's eyes corresponding to the given time instant, based on the plurality of tracking parameters determined from the given image;

generating a set of uncalibrated gaze vectors of the user's eyes corresponding to the plurality of time instants, by performing said processing and said estimation for each of the plurality of images;

storing at least temporarily the uncalibrated gaze vectors of the set along with corresponding time instants and corresponding pluralities of tracking parameters;

selecting, a first subset of uncalibrated gaze vectors from amongst the set of uncalibrated gaze vectors whose direction matches with a predefined forward axis of vision;

fetching corresponding pluralities of tracking parameters for the uncalibrated gaze vectors of the first subset;

determining a maximum distance between the irises of the user's eyes, based on the corresponding pluralities of tracking parameters fetched for the uncalibrated gaze vectors of the first subset; and considering the maximum distance as an interpupillary distance of the user for focusing distances greater than a predefined threshold distance.

The present disclosure provides the aforementioned system and the aforementioned method which facilitate a simple, yet accurate, reliable, and implicit way to calibrate uncalibrated gaze vectors and a focusing distance of user's eyes, in a time-efficient and computationally-efficient manner. Herein, for the first subset of the uncalibrated gaze vectors whose direction matches with the predefined forward axis of vision (i.e., when the user is looking straight ahead within his/her field of view), the maximum distance between the irises is determined on-the-fly, by way of utilising the pluralities of tracking parameters. Thus, the maximum distance is considered as an interpupillary distance of the user, and for the focusing distances greater than the predefined threshold distance (for example, such as 10 metres), calibrated gaze vectors can be accurately estimated. Beneficially, this eliminates a need for the user to perform explicit calibration tasks, which typically require dedicated calibration procedures and user instructions (for example, such as focusing on specific dots or features) as in the case of prior art, which consume time and effort of the user, and can disrupt his/her primary tasks, such as driving. The system and the method are simple, robust, fast, reliable, support real-time implicit gaze and focus distance calibration, and can be implemented with ease.

Notably, the at least one processor controls an overall operation of the system. The at least one processor is communicably coupled to at least the at least one tracking camera. In some implementations, the at least one processor is implemented as a processor of a computing device. Examples of the computing device include, but are not limited to, a laptop, a tablet, a phablet, and a smartphone. In other implementations, the at least one processor is implemented as a cloud server (namely, a remote server) that provides a cloud computing service.

Throughout the present disclosure, the term "tracking camera" refers to a specialised equipment for detecting and/or following the user's face, in order to capture a given image of the user's face at a given time instant. It is to be noted that the plurality of images are captured by the at least one tracking camera at different time instants, i.e., the plurality of images are not captured simultaneously. It will be appreciated that the at least one tracking camera is arranged to face the user, when the system is being used, in order to facilitate capturing the plurality of images of the user's face.

Optionally, the at least one tracking camera comprises at least one of: at least one visible-light camera, at least one infrared (IR) camera, at least one depth camera. Examples of a given visible-light camera include, but are not limited to, a Red-Green-Blue (RGB) camera, a Red-Green-Blue-Alpha (RGB-A) camera, a Red-Green-Blue-Depth (RGB-D) camera, a Red-Green-Blue-White (RGBW) camera, a Red-Green-Blue-Infrared (RGB-IR) camera, and a monochrome camera. Examples of a given depth camera include, but are not limited to, a Time-of-Flight (ToF) camera, a light detection and ranging (LiDAR) camera, a Red-Green-Blue-Depth (RGB-D) camera, a laser rangefinder, a stereo camera, a plenoptic camera, and a Sound Navigation and Ranging (SONAR) camera. It will be appreciated that any combination of various different types of cameras (for example, such as the at least one visible-light camera, the at least one IR camera, and the at least one depth camera) may be utilised in the at least one tracking camera. When different types of images captured by the various different types of cameras are utilised, the plurality of tracking parameters could be determined with high accuracy, as results obtained from one type of image can be used to refine results obtained from another type of image. Herein, these different types of images constitute tracking data collected by the at least one tracking camera, wherein said tracking data may be in the form of at least one of: visible-light images, IR images, depth images.

It will be appreciated that the given image is a visual representation of the user's face from a perspective of a given pose of the at least one tracking camera at the given time instant. It is to be understood that the given image may not only represent the user's face, but may also represent other part(s) of the user's body and other real-world objects present in surroundings of the user. The term "pose" encompasses at least one of: a viewing position, a viewing direction. The term "visual representation" encompasses colour information represented in the given image, and additionally optionally other attributes associated with the given image (for example, such as depth information, luminance information, transparency information, and the like). Optionally, the colour information represented in the given image is in form of at least one of: Red-Green-Blue (RGB) values, Red-Green-Blue-Alpha (RGB-A) values, Cyan-Magenta-Yellow-Black (CMYK) values, Luminance and two-colour differences (YUV) values, Red-Green-Blue-Depth (RGB-D) values.

Notably, the given image is processed to determine the plurality of tracking parameters. Throughout the present disclosure, the term "tracking parameter" refers to a trackable characteristic of the user's body. Optionally, when processing the given image (captured at the given time instant), the at least one processor is configured to: extract a plurality of features from the given image; and identify the user's head, the user's eyes, the eyeballs of the user's eyes, and at least one of: the irises of the user's eyes, the boundaries of the eyeballs, the corners of the user's eyes, the shapes of the user's eyes, based on the plurality of extracted features. Optionally, a given tracking parameter from amongst the plurality of tracking parameters is represented in a given coordinate space. As an example, the given coordinate space may be a Cartesian coordinate space. Examples of the features include, but are not limited to, edges, lines, corners, blobs and ridges. It will be appreciated that for performing the aforesaid extraction of the features and the aforesaid identification, the at least one processor is optionally configured to employ at least one of: at least one facial landmark detection algorithm, at least one feature extraction algorithm. Examples of the at least one facial landmark detection algorithm include, but are not limited to, a 68-point face landmark algorithm, a multi-task cascaded convolutional neural network (MTCNN)-based algorithm. Examples of the at least one feature extraction algorithm include, but are not limited to, an edge-detection algorithm (for example, such as Canny edge detector, Deriche edge detector, and the like), a corner-detection algorithm (for example, such as Harris & Stephens corner detector, Shi-Tomasi corner detector, Features from Accelerated Segment Test (FAST) corner detector, and the like), a blob-detection algorithm (for example, such as Laplacian of Gaussian (LoG)-based blob detector, Difference of Gaussians (DoG)-based blob detector, Maximally Stable Extremal Regions (MSER) blob detector, and the like), a line-detection algorithm (for example, such as a standard Hough transform line detector, a probabilistic Hough transform line detector, an extended Hough transform line detector, a line segment detector (LSD) algorithm, and the like), a feature descriptor algorithm (for example, such as Binary Robust Independent Elementary Features (BRIEF), Gradient Location and Orientation Histogram (GLOH), Histogram of Oriented Gradients (HOG), and the like), and a feature detector algorithm (for example, such as Scale-Invariant Feature Transform (SIFT), Oriented FAST and rotated BRIEF (ORB), Speeded Up Robust Features (SURF), and the like). All the aforementioned algorithms are well-known in the art. Moreover, the aforesaid identification could also be performed using at least one object detection algorithm and at least one object segmentation algorithm, to isolate a relevant part of the given image from its background. The shapes of the user's eyes may be defined by epicanthic folds of the user's eyes.

Throughout the present disclosure, the term "gaze vector" of a given eye of the user refers to a vector that is indicative of a gaze direction of the given eye of the user. Throughout the present disclosure, the term "uncalibrated gaze vector" of the given eye of the user refers to a gaze vector that has not been adjusted or calibrated for enhanced accuracy. It will be appreciated that any uncalibrated gaze vector provides a preliminary (namely, raw) estimation of the gaze direction of the given eye, lacking any refinement or fine-tuning for enhanced accuracy. Thus, the uncalibrated gaze vector may not perfectly align with an exact gaze direction of the given eye, and may be interpreted with an understanding that it may not be as precise as a calibrated gaze vector.

It will also be appreciated that the pose of the user's head provides a viewing position of the user and a viewing direction in which the user is facing within his/her surroundings at the given time instant. Moreover, the positions of the eyeballs of the user's eyes and the at least one of: the relative positions of the irises with respect to the boundaries of the eyeballs, the relative positions of the irises with respect to the corners of the user's eyes, the shapes of the user's eyes, facilitate in determining orientations of the irises (namely, directions in which the user's eyes are pointing), thereby providing information pertaining to where the user is likely looking/gazing within his/her field of view at the given time instant. In an example, when an eyeball of a left eye of the user is turned slightly towards the user's nose (namely, towards a right side), while an eyeball of a right eye of the user is turned slightly outward (namely, towards the right side), it may be estimated that the user is gazing towards a right region within his/her field of view. In another example, when the user's eyeballs turn such that the irises of the user's eyes come closer towards lower boundaries of the eyeballs, it may be estimated that the user is gazing towards a bottom region within his/her field of view. In yet another example, when an iris of a right eye of the user is closer to an outer corner of the right eye, while an iris of a left eye of the user is closer to an inner corner of the left eye, it may be estimated that the user is gazing towards a top-right region within his/her field of view. In still another example, when the user squints, shapes of both the eyes of the user become narrower and more elongated in a horizontal direction, thereby altering an appearance of eyelids of the user's eyes and an overall contour of the user's eyes. In this way, by utilising the plurality of tracking parameters, the at least one processor can easily ascertain a comprehensive understanding of a user's gaze at the given time instant. Therefore, the at least one processor could easily estimate the uncalibrated gaze vectors of the user's eyes corresponding to the given time instant. Techniques for estimating gaze vectors of the user's eyes by utilising such tracking parameters are well-known in the art.

Since the user's gaze may change continuously when the system is being used, different uncalibrated gaze vectors of the user's eyes are estimated corresponding to different time instants, by processing the plurality of images in a similar manner, as described hereinabove in detail. In this regard, the set of uncalibrated gaze vectors is generated. It will be appreciated that said (single and overall) set would comprise the uncalibrated gaze vectors corresponding to different scenarios, for example, such as when the user is gazing towards at least one of: a central region, a top region, a bottom region, a left region, a right region, a top-left region, a bottom-right region, a top-right region, a bottom-left region, within his/her field of view. Thus, in such a case, uncalibrated gaze vectors that correspond to a same region of the field of view of the user would have similar directions.

Optionally, the uncalibrated gaze vectors of said set are at least temporarily stored along with the corresponding time instants and the corresponding pluralities of tracking parameters, at a data repository communicably coupled to the at least one processor. It will be appreciated that the data repository could, for example, be implemented as a memory of the at least one processor, a memory of the at least one tracking camera, a memory of the computing device, a removable memory, a cloud-based database, or similar. Optionally, the system further comprises the data repository.

Throughout the present disclosure, the term "forward axis of vision" refers to an imaginary line extending from an average position of the user's eyes (that corresponds to a viewing position of the user's head) in a direction that aligns with a line of sight of the user when the user is looking straight ahead within his/her field of view. Different users would have different forward axes of vision due to various factors, for example, such as different heights, different body postures, and other anatomical differences.

It will be appreciated that the predefined forward axis of vision could be predefined based on a use case. In an example implementation, when the user is present inside a vehicle and is driving the vehicle, the predefined forward axis of vision could be predefined to be parallel to a longitudinal axis of the vehicle. In such an implementation, it can be understood that the forward axis of vision would align with a direction in which the vehicle is moving and would correspond to the line of sight of the user while the user is looking straight ahead from his/her seating position in the vehicle. Moreover, the forward axis of vision may not be perfectly straight, and may likely be slightly angled in a downward direction relative to a horizontal plane. This is due to the fact that when the user is driving the vehicle, the user would typically focus his/her gaze on a road ahead, rather than looking towards the sky or windows of the vehicle. As a result, the forward axis of vision tends to be oriented slightly downward relative to the horizontal plane. The vehicle could, for example, be a car, a truck, an aircraft, a speed boat or the like. The car could be a convertible car or a hardtop car. The vehicle could also be a semi-open vehicle (such as a boat). As another example, when the user is present inside a vehicle, the forward axis of vision may also be defined based on an orientation of a torso of the user's body, because the user will most likely be sitting straight inside the vehicle, and will not be twisting inside the vehicle, while the system is being used. Moreover, since the torso of the user's body is relatively large in size as compared to the user's eyes, the torso can be easily tracked by using the at least one tracking camera. It will be appreciated that when the user is present in the vehicle, the uncalibrated gaze vectors of the first subset would likely be accumulated when said vehicle is in motion, as when the vehicle is stationary (for example, when the user is waiting for a traffic light), the user's gaze may drift as he/she focusses on peripheral object(s) in his/her surroundings, however, a number of such type of uncalibrated gaze vectors is likely smaller.

Notably, the first subset of uncalibrated gaze vectors comprises only those uncalibrated gaze vectors whose direction matches with the predefined forward axis of vision. In this regard, uncalibrated gaze vectors (from amongst said set) that correspond to a scenario, for example, such as when the user is gazing towards the central region within his/her field of view, are selected to be included in the first subset. This may, particularly, be applicable when the user is driving the vehicle. While driving the vehicle, a gaze of the user's eyes may likely be towards a central region within a field of view of the user, as the user is likely gazing towards object(s) (for example, such as a road or a tree adjacent to a road) located at a distance greater than the predefined threshold distance (for example, such as 10 meters). In other words, the user is gazing towards far object(s). Since information pertaining to the uncalibrated gaze vectors of said set is already and accurately known to the at least one processor, the first subset could be easily selected by the at least one processor. It will be appreciated that there may be some uncalibrated gaze vectors in said set whose directions exactly match with the predefined forward axis of vision. However, there may also be other uncalibrated gaze vectors in said set whose directions somewhat match (namely, match to some extent) with the predefined forward axis of vision. In other words, there may not always be a perfect match between directions of uncalibrated gaze vectors and the predefined forward axis of vision. Therefore, in this regard, the at least one processor is optionally configured to select those uncalibrated gaze vectors from amongst said set whose directions lie within a predefined angle from the predefined forward axis of vision, wherein said selected uncalibrated gaze vectors are (also) included in the first subset. Optionally, the predefined angle lies in a range of 0 degree to 5 degrees. It is to be understood that the predefined angle would be 0 degree in case of an exact match between a direction of an uncalibrated gaze vector in said set and the predefined forward axis of vision.

It will be appreciated that for estimating calibrated gaze vectors of the user's eyes corresponding to any given time instant, the at least one processor may be configured to take into account information pertaining to negative zones in the enclosed space where the user is unlikely to gaze. When the enclosed space is a cabin of the vehicle, said negative zones may, for example, comprise A-pillar of the vehicle, a top of a dashboard of the vehicle, and the like. Moreover, these negative zones are specific to a vehicle scenario only. There could be instruments at which the user may be looking. For example, in case of aviation, there are instruments on a top part of the field of view of the user also.

Once the uncalibrated gaze vectors of the first subset are known, the corresponding pluralities of tracking parameters are fetched by the at least one processor, for example, from the data repository. Since the first subset comprises the uncalibrated gaze vectors whose direction matches with the predefined forward axis of vision, it may be highly likely that said uncalibrated gaze vectors correspond to the object (s) located at the distance greater than the predefined threshold distance (as discussed earlier). In this regard, a distance between the irises of the user's eyes would likely be maximum. This is due to the fact that when the user focusses on a nearby object (namely, an object located at a distance less than the predefined threshold distance), pupils of the user's eyes constricts, causing a slight decrease in the distance between the irises of the user's eyes, and also in the interpupillary distance. Conversely, when the user focusses on a far object, pupils of the user's eyes dilate to allow additional light to enter the user's eyes. Such a dilation of the pupils results in a slight increase in the distance between the irises of the user's eyes, and also in the interpupillary distance. When said far object is assumed to be located at infinity or near-infinity, there would be a maximum distance between the irises of the user's eyes. It will be appreciated that since positions of the eyeballs, and at least one of: relative positions of the irises with respect to the boundaries of the eyeballs, relative positions of the irises with respect to the corners of the user's eyes, are already and accurately known (as the corresponding pluralities of tracking parameters for the first subset are known), the at least one processor could easily determine the maximum distance between the irises of the user's eyes, for example, by utilising a coordinate geometry-based technique and/or a trigonometry-based technique.

Notably, for the focusing distances greater than the predefined threshold distance, the (determined) maximum distance is considered as the interpupillary distance (IPD) of the user. Throughout the present disclosure, the term "focusing distance" refers to a distance between the user's eyes and a given object at which the user's gaze is focused. Throughout the present disclosure, the term "interpupillary distance" refers to an actual distance between pupils of the user's eyes when the user is looking at a given focusing distance. Greater the focusing distance of the user, greater is the IPD of the user, and vice versa. For example, an IPD corresponding to a focusing distance of 10 meters is more than an IPD corresponding to a focusing distance of 1 meter.

Optionally, the at least one processor is configured to:

generate a mapping between a forward axis of vision specific to the user and the corresponding pluralities of tracking parameters fetched for the uncalibrated gaze vectors of the first subset; and estimate calibrated gaze vectors of the user's eyes corresponding to a next time instant, based on a plurality of tracking parameters determined from a next image captured at the next time instant, by utilising the generated mapping.

In this regard, since the forward axis of vision specific to the user and the corresponding pluralities of tracking parameters are already and accurately known, the at least one processor can easily generate said mapping, for example, by identifying a correlation between the corresponding pluralities of tracking parameters and the forward axis of vision. In an example, for generating said mapping, the at least one processor may associate different combinations of tracking parameters (fetched for the uncalibrated gaze vectors of the first subset) with the forward axis of vision. Thus, the at least one processor can easily perform calibration of subsequent gaze vectors of the user's eyes (corresponding to the next time instant), by utilising the generated mapping. For example, when similar combination(s) of tracking parameters is/are determined from the next image, the at least one processor can utilise the generated mapping to ascertain that the user's gaze is likely along the forward axis of vision, and thus can accurately estimate the calibrated gaze vectors of the user's eyes accordingly. Performing calibrations by utilising a mapping is well-known in the art. It will be appreciated that estimating the calibrated gaze vectors using the uncalibrated gaze vectors may enable in accurately determining an optical axis of a given eye of the user, wherein said optical axis represents a principal direction in which light travels through the given eye when focused on an object. Understanding said optical axis is crucial in gaze tracking because it helps in determining the direction in which the eye is looking. While an orientation of the iris can provide a rough estimate of the optical axis, achieving a high tracking accuracy requires specifically targeting the optical axis.

It will be appreciated that a mapping could be generated in form of a data structure (for example, such as a lookup table), a database, or could be learned and stored in the form of a machine learning model. The mapping could also be stored in a text-based file format or comma-separated values (CSV)-based file format. It is to be noted that the mapping is specific to the user i.e., for different users, different mappings are generated by the at least one processor in a similar manner, as described earlier.

The technical benefit of estimating the calibrated gaze vectors in the aforesaid manner is that it facilitates in performing an implicit gaze calibration which eliminates a need for users to perform explicit calibration tasks, which typically require dedicated calibration procedures and user instructions (for example, such as focusing on specific dots or features) as in the case of prior art. Performing such explicit calibration tasks also consume time and effort of the users, and can disrupt their primary tasks, such as driving. Thus, by seamlessly calibrating gaze vectors in the background without user intervention, the system automatically adapts to user's gaze behaviour over time, eliminating a need for repetitive, time-consuming, explicit calibration tasks. In this way, an overall accuracy of gaze tracking of the user's eyes is significantly improved.

Optionally, the at least one processor is configured to:

detect an input event pertaining to a selection of an input option by the user;

when the input event is detected, determine a position of the input option selected by the user and a time instant at which the input option was selected by the user;

select, from amongst the set of uncalibrated gaze vectors, a second subset of uncalibrated gaze vectors whose corresponding time instants lie within a predefined time period from the time instant at which the input option was selected by the user, and whose direction matches with viewing directions pointing from the positions of the eyeballs towards the position of the input option;

for the uncalibrated gaze vectors of the second subset, fetch corresponding pluralities of tracking parameters; and determine a focusing distance of the user's eyes corresponding to when the user is looking at the input option, based on a distance between the position of the input option and the positions of eyeballs of the user's eyes in the corresponding pluralities of tracking parameters fetched for the uncalibrated gaze vectors of the second subset.

The term "input event" refers to an incidence of the user selecting the input option. It will be appreciated that said input option could, for example, be selected at a given input device. In an example, when the given input device is a display, the input option could be a virtual option being displayed at the display, and the input event could be touching said virtual option. In another example, when the given input device is an air conditioner control panel, the input option could be a physical button at the air conditioner control panel, and the input event could be pressing said physical button. Optionally, the at least one processor is configured to detect an occurrence of the input event at the given input device upon receiving, from the given input device, a signal corresponding to the selection of the input option by the user, wherein the at least one processor is communicably coupled to the given input device.

Optionally, the at least one processor is configured to determine the position of the input option by utilising at least one of: a three-dimensional (3D) model of the user's surroundings that is pre-generated and pre-stored at the data repository, a pre-known location of the given input device. In an example, the at least one processor may identify a location of a region of interest within the user's surroundings whereat the user is focusing or is more likely to focus, by utilising the 3D model of the user's surroundings, and utilise said location of the region of interest to determine the position of the input option. Further, since the at least one processor detects the occurrence of the input event, the time instant at which the input option was selected by the user is accurately known to the at least one processor itself.

It will be appreciated that prior to selecting the input option and even upon selecting the input option, it may be likely that the user momentarily looks/gazes at the input option. This may, particularly, be applicable in a scenario where the user is driving the vehicle, and may press a physical button at an input device arranged inside the vehicle. Thus, in such a case, those uncalibrated gaze vectors in said set whose corresponding time instants lie within the predefined time period (for example, such as (+/−) 2 seconds from the time instant) would be selected in the second subset, because said uncalibrated gaze vectors correspond to a scenario where the user is highly likely looking at the input option. Additionally, those uncalibrated gaze vectors in said set whose directions match with the aforesaid viewing directions would be selected in the second subset, as said uncalibrated gaze vectors correspond to the scenario where the user is highly likely looking at the input option. Since the positions of the eyeballs and the position of the input option are known, the aforesaid viewing directions could be easily determined by the at least one processor, for example, by mapping a vector from a position of a given eyeball towards the position of the input option.

Once the uncalibrated gaze vectors of the second subset are known, the corresponding pluralities of tracking parameters are fetched by the at least one processor, for example, from the data repository. It will be appreciated that when the user is looking at the input option, the focusing distance of the user's eyes can be understood to be the distance between the position of the input option and the positions of eyeballs of the user's eyes. Since the position of the input option and the positions of eyeballs of the user's eyes are already and accurately known, the distance can be easily determined, for example, by utilising a coordinate geometry-based technique. Advantageously, in this manner, the focusing distance of the user's eyes corresponding to when the user is looking at the input option is determined implicitly and with a high accuracy. This subsequently facilitates in improving an accuracy of gaze tracking of the user's eyes. For example, when the user presses a physical button or a virtual button, he/she is typically looking at it to ensure that he/she has selected a correct/intended input option. Such a behaviour provides a valuable opportunity for calibrating the user's gaze vectors. This may, particularly, be useful for aligning any uncalibrated gaze vectors that are roughly directed towards the physical button or the virtual button, enhancing the accuracy of gaze tracking of the user's eyes.

Optionally, the at least one processor is configured to:

determine a distance between the irises of the user's eyes, based on the corresponding pluralities of tracking parameters fetched for the uncalibrated gaze vectors of the second subset; and consider the distance as an interpupillary distance of the user for the focusing distance of the user's eyes corresponding to when the user is looking at the input option.

In this regard, when the user is looking at the input option, it can be understood that the uncalibrated gaze vectors of the second subset correspond to an object that is located relatively near to the user (i.e., at a distance less than the predefined threshold distance). In this regard, the distance between the irises of the user's eyes would be less than the maximum distance. It will be appreciated that since positions of the eyeballs, and at least one of: relative positions of the irises with respect to the boundaries of the eyeballs, relative positions of the irises with respect to the corners of the user's eyes, are already and accurately known (as the corresponding pluralities of tracking parameters for the second subset are known), the at least one processor could easily determine the distance between the irises of the user's eyes, for example, by utilising a coordinate geometry-based technique and/or a trigonometry-based technique. Therefore, for the focusing distance corresponding to when the user is looking at the input option, the (determined) distance is considered as the IPD of the user.

Optionally, the at least one processor is configured to:

generate a mapping between the viewing directions pointing from the positions of the eyeballs towards the position of the input option, and the corresponding pluralities of tracking parameters fetched for the uncalibrated gaze vectors of the second subset; and estimate calibrated gaze vectors of the user's eyes corresponding to another next time instant, based on a plurality of tracking parameters determined from another next image captured at the another next time instant, by utilising the generated mapping.

In this regard, since the aforesaid viewing directions and the corresponding pluralities of tracking parameters for the second subset are already and accurately known, the at least one processor can easily generate said mapping, for example, by identifying a correlation between said corresponding pluralities of tracking parameters and the aforesaid viewing directions. In an example, for generating said mapping, the at least one processor may associate different combinations of tracking parameters (fetched for the uncalibrated gaze vectors of the second subset) with the aforesaid viewing directions. Thus, the at least one processor can easily perform calibration of subsequent gaze vectors of the user's eyes (corresponding to the another next time instant), by utilising the generated mapping. For example, when similar combination(s) of tracking parameters is/are determined from the another next image, the at least one processor can utilise the generated mapping to ascertain that the user's gaze is likely along any of the aforesaid viewing directions, and thus can accurately estimate the calibrated gaze vectors of the user's eyes accordingly. Performing calibrations by utilising a mapping is well-known in the art. In an example, the user may press a physical button which controls a seat warmer. In such a case, when the at least one processor utilises the mapping, 15 uncalibrated gaze vectors may be identified immediately before occurrence of said input event, which when projected against a static 3D model of an interior of vehicle, are identified to be within 10 centimetres of a location of the physical button determined from the static 3D model.

The technical benefit of estimating the calibrated gaze vectors in the aforesaid manner is that it facilitates in performing an implicit gaze calibration which eliminates a need for users to perform explicit calibration tasks, which typically require dedicated calibration procedures and user instructions (for example, such as focusing on specific dots or features), which consume time and effort of the users, and can disrupt their primary tasks, such as driving. Thus, by seamlessly calibrating gaze vectors in the background without user intervention, the system automatically adapts to user's gaze behaviour over time, eliminating a need for repetitive calibration tasks.

Optionally, the system is implemented in an enclosed space in which at least one instrument is being used, wherein the at least one processor is configured to:

select, from amongst the set of uncalibrated gaze vectors, a third subset of uncalibrated gaze vectors whose direction matches with viewing directions pointing from the positions of the eyeballs towards a position of the at least one instrument;

for the uncalibrated gaze vectors of the third subset, fetch corresponding pluralities of tracking parameters; and determine a focusing distance of the user's eyes corresponding to when the user is looking at the at least one instrument, based on a distance between the position of the at least one instrument and the positions of eyeballs of the user's eyes in the corresponding pluralities of tracking parameters fetched for the uncalibrated gaze vectors of the third subset.

The term "enclosed space" refers to a physical space that is at least partially surrounded by boundaries or coverings. In other words, the enclosed space could either be a partially enclosed space or a fully enclosed space. Optionally, the enclosed space is in a form of a cabin of a vehicle. It is to be understood that when the enclosed space is the cabin of the vehicle, the user sitting on a seat of the vehicle could be a driver of the vehicle or a passenger in the vehicle. It will be appreciated that the enclosed space may also be located in a museum, a monument, an entertainment park, or the like. It will also be appreciated that the at least one tracking camera could be utilised inside an enclosed space that is rigid. Herein, the term "rigid" refers to only a structural rigidity of the enclosed space. The enclosed space could be movable/portable.

In some implementations, the at least one instrument could be a physical instrument, for example, such as a machine's bucket for an excavator, a factory equipment, a control room equipment, and the like. In other implementations, the at least one instrument could be an instrument in a vehicle, for example, such as a speedometer, a fuel indicator, a temperature indicator, an odometer, a pressure indicator, and the like, of the vehicle. It will be appreciated that the at least one instrument need not necessarily be arranged inside the enclosed space, i.e., the at least one instrument could be arranged outside the enclosed space.

It will be appreciated that those uncalibrated gaze vectors in said set whose directions match with the aforesaid viewing directions would be selected in the third subset, as said uncalibrated gaze vectors correspond to a scenario where the user is highly likely looking at the at least one instrument. In some cases, the position of the at least one instrument is pre-known to the at least one processor. In other cases, the at least one processor is configured to determine the position of the at least one instrument by utilising a 3D model of the enclosed space, wherein the 3D model of the enclosed space is pre-generated and pre-stored at the data repository. Since the positions of the eyeballs and the position of the at least one instrument are known, the aforesaid viewing directions could be easily determined by the at least one processor, for example, by mapping a vector from a position of a given eyeball towards the position of the at least one instrument.

Once the uncalibrated gaze vectors of the third subset are known, the corresponding pluralities of tracking parameters are fetched by the at least one processor, for example, from the data repository. It will be appreciated that when the user is looking at the at least one instrument, the focusing distance of the user's eyes can be understood to be the distance between the position of the at least one instrument and the positions of eyeballs of the user's eyes. Since the position of the at least one instrument and the positions of eyeballs of the user's eyes are already and accurately known, the distance can be easily determined, for example, by utilising a coordinate geometry-based technique. Advantageously, in this manner, the focusing distance of the user's eyes corresponding to when the user is looking at the at least one instrument is determined implicitly and with a high accuracy. This subsequently facilitates in improving an accuracy of gaze tracking of the user's eyes. For example, when the user uses the at least one instrument in the enclosed space, he/she typically looks at it to ensure that he/she is using it in an intended manner. Such a behaviour provides a valuable opportunity for calibrating the user's gaze vectors. This may, particularly, be useful for aligning any uncalibrated gaze vectors that are roughly directed towards at least one instrument, enhancing the accuracy of gaze tracking of the user's eyes.

Optionally, the at least one processor is configured to:

determine a distance between the irises of the user's eyes, based on the corresponding pluralities of tracking parameters fetched for the uncalibrated gaze vectors of the third subset; and consider the distance as an interpupillary distance of the user for the focusing distance of the user's eyes corresponding to when the user is looking at the at least one instrument.

In this regard, when the user is looking at the at least one instrument, it can be understood that the uncalibrated gaze vectors of the third subset correspond to at least one object that is located relatively near to the user (i.e., at a distance less than the predefined threshold distance). In this regard, the distance between the irises of the user's eyes would be less than the maximum distance. It will be appreciated that since positions of the eyeballs, and at least one of: relative positions of the irises with respect to the boundaries of the eyeballs, relative positions of the irises with respect to the corners of the user's eyes, are already and accurately known (as the corresponding pluralities of tracking parameters for the third subset are known), the at least one processor could easily determine the distance between the irises of the user's eyes, for example, by utilising a coordinate geometry-based technique and/or a trigonometry-based technique. Therefore, for the focusing distance corresponding to when the user is looking at the at least one instrument, the (determined) distance is considered as the IPD of the user.

It will also be appreciated that for any focusing distance of the user's eyes less than the predefined threshold distance (for example, as discussed earlier for scenarios when the user is looking at the input option and when the user is looking at the at least one instrument), when significant number of images of the user's face have been captured and processed in a similar manner as described earlier, the at least one processor is optionally configured to derive a user-specific IPD equation. The user-specific IPD equation could be derived, for example, such as in the form of a logarithmic equation or a polynomial equation. Said user-specific IPD equation can be conveniently utilised for predicting a focusing distance of the user's eyes, based on a given IPD of the user's eyes. Beneficially, different user-specific IPD equations facilitate in improving an accuracy of gaze tracking for different users for which the different user-specific IPD equations are derived, as compared to a scenario where a same, generic IPD equation is to be utilised for all the different users.

Optionally, the at least one processor is configured to:

generate a mapping between the viewing directions pointing from the positions of the eyeballs towards the position of the at least one instrument, and the corresponding pluralities of tracking parameters fetched for the uncalibrated gaze vectors of the third subset; and estimate calibrated gaze vectors of the user's eyes corresponding to yet another next time instant, based on a plurality of tracking parameters determined from yet another next image captured at the yet another next time instant, by utilising the generated mapping.

In this regard, since the aforesaid viewing directions and the corresponding pluralities of tracking parameters for the third subset are already and accurately known, the at least one processor can easily generate said mapping, for example, by identifying a correlation between said corresponding pluralities of tracking parameters and the aforesaid viewing directions. In an example, for generating said mapping, the at least one processor may associate different combinations of tracking parameters (fetched for the uncalibrated gaze vectors of the third subset) with the aforesaid viewing directions. Thus, the at least one processor can easily perform calibration of subsequent gaze vectors of the user's eyes (corresponding to the yet another next time instant), by utilising the generated mapping. For example, when similar combination(s) of tracking parameters is/are determined from the yet another next image, the at least one processor can utilise the generated mapping to ascertain that the user's gaze is likely along any of the aforesaid viewing directions, and can accurately estimate the calibrated gaze vectors of the user's eyes accordingly. Beneficially, the calibrated gaze vectors are highly accurately estimated in terms of indicating a gaze direction of the user's eyes when the user is looking at the at least one instrument at the yet another next time instant. Performing calibrations by utilising a mapping is well-known in the art. The technical benefit of estimating the calibrated gaze vectors in the aforesaid manner is that it facilitates in performing an implicit gaze calibration which eliminates a need for users to perform explicit calibration tasks, as discussed earlier in detail.

Optionally, the system is implemented in a vehicle, wherein the system further comprises at least one real-world-facing camera, and wherein the at least one processor is configured to:

- process images captured by the at least one real-world-facing camera, to generate a depth image of the real-world environment;
- reproject the depth image of the real-world environment from a perspective of the at least one real-world facing camera to a perspective of a position of a given eye of the user; and
- for the uncalibrated gaze vectors of the first subset, determine a focusing distance of the user's eyes corresponding to a forward axis of vision specific to the user, by utilising the reprojected depth image.

The term "real-world-facing camera" refers to a camera that is arranged to face the real-world environment, and is employed to capture images of the real-world environment. The at least one real-world-facing camera could comprise at least one of: at least one visible-light camera, at least one depth camera. Thus, said images could be depth images and/or visible-light images of the real-world environment. As an example, the images may be captured as RGB-D images. In case of visible-light cameras, the depth image can be generated based on a stereo disparity between images captured by a pair of visible-light cameras. Herein, the term "depth image" refers to an image comprising information pertaining to optical depths of objects or their portions present in the real-world environment. In other words, the depth image provides information pertaining to distances (namely, the optical depths) of surfaces of the objects or their portions, from a perspective of a pose of the at least one real-world-facing camera. It is to be understood that depth images would also be indicative of placements, geometries, occlusions, and the like, of the real-world objects from various perspectives of poses of the at least one real-world-facing camera.

Optionally, when reprojecting the depth image, the at least one processor is configured to employ at least one image reprojection algorithm. The at least one image reprojection algorithm comprises at least one space warping algorithm. Image reprojection algorithms are well-known in the art. It will be appreciated that since the perspective of the at least one real-world facing camera and the perspective of the position of the given eye are different, and for the depth image to be utilised to determine the focusing distance of the user's eyes, the at least one processor reprojects the depth image to match the perspective of the position of the given eye. Thus, the reprojected depth image represents the optical depths of objects or their portions from the perspective of the position of the given eye. In this regard, for each uncalibrated gaze vector of the first subset, the reprojected depth image can be conveniently utilised by the at least one processor to determine the focusing distance, for example, by mapping each uncalibrated gaze vector onto the depth image. The depth value retrieved from the depth image at coordinates corresponding to each uncalibrated gaze vector is determined as the focusing distance of the user's eyes. Determining the focusing distance for the uncalibrated gaze vectors of the first subset in the aforesaid manner (namely, by using the depth image) is simple, reliable, and highly accurate. This subsequently facilitates in improving an accuracy of gaze tracking of the user's eyes. This may be because optical depths of several different objects from the perspective of the position of the given eye provide a reliable reference point (namely, a ground truth), for determining a focusing distance of an object that the user is likely to have looked at. Such an approach may, particularly, be beneficial when estimating the user's gaze direction for far-field distances (for example, such as in a range of 2 metres to 10 metres). While near-field gaze estimation is easier due to more noticeable pupil movement of the user's eyes and strong depth cues within the vehicle, calibration for far-field gaze estimation requires an additional certainty. Thus, by utilising the reprojected depth image, this approach may provide a more precise determination of the focusing distance of the user's eyes. Such an additional certainty is crucial for constructing an accurate curve fit for gaze estimation over relatively long distances, thereby enhancing an overall accuracy and reliability of the gaze tracking.

The present disclosure also relates to the method as described above. Various embodiments and variants disclosed above, with respect to the aforementioned first aspect, apply mutatis mutandis to the method.

Optionally, the method further comprises:

- generating a mapping between a forward axis of vision specific to the user and the corresponding pluralities of tracking parameters fetched for the uncalibrated gaze vectors of the first subset; and
- estimating calibrated gaze vectors of the user's eyes corresponding to a next time instant, based on a plurality of tracking parameters determined from a next image captured at the next time instant, by utilising the generated mapping.

Optionally, the method further comprises:

- detecting an input event pertaining to a selection of an input option by the user;
- when the input event is detected, determining a position of the input option selected by the user and a time instant at which the input option was selected by the user;
- selecting, from amongst the set of uncalibrated gaze vectors, a second subset of uncalibrated gaze vectors whose corresponding time instants lie within a predefined time period from the time instant at which the input option was selected by the user, and whose direction matches with viewing directions pointing from the positions of the eyeballs towards the position of the input option;

fetching corresponding pluralities of tracking parameters for the uncalibrated gaze vectors of the second subset; and determining a focusing distance of the user's eyes corresponding to when the user is looking at the input option, based on a distance between the position of the input option and the positions of eyeballs of the user's eyes in the corresponding pluralities of tracking parameters fetched for the uncalibrated gaze vectors of the second subset.

Optionally, the method further comprises:

determining a distance between the irises of the user's eyes, based on the corresponding pluralities of tracking parameters fetched for the uncalibrated gaze vectors of the second subset; and considering the distance as an interpupillary distance of the user for the focusing distance of the user's eyes corresponding to when the user is looking at the input option.

Optionally, the method further comprises:

generating a mapping between the viewing directions pointing from the positions of the eyeballs towards the position of the input option, and the corresponding pluralities of tracking parameters fetched for the uncalibrated gaze vectors of the second subset; and estimating calibrated gaze vectors of the user's eyes corresponding to another next time instant, based on a plurality of tracking parameters determined from another next image captured at the another next time instant, by utilising the generated mapping.

Optionally, the method further comprises:

selecting, from amongst the set of uncalibrated gaze vectors, a third subset of uncalibrated gaze vectors whose direction matches with viewing directions pointing from the positions of the eyeballs towards a position of at least one instrument, wherein the at least one instrument is being used in an enclosed space;

fetching corresponding pluralities of tracking parameters for the uncalibrated gaze vectors of the third subset; and determining a focusing distance of the user's eyes corresponding to when the user is looking at the at least one instrument, based on a distance between the position of the at least one instrument and the positions of eyeballs of the user's eyes in the corresponding pluralities of tracking parameters fetched for the uncalibrated gaze vectors of the third subset.

Optionally, the method further comprises:

determining a distance between the irises of the user's eyes, based on the corresponding pluralities of tracking parameters fetched for the uncalibrated gaze vectors of the third subset; and considering the distance as an interpupillary distance of the user for the focusing distance of the user's eyes corresponding to when the user is looking at the at least one instrument.

Optionally, the method further comprises:

generating a mapping between the viewing directions pointing from the positions of the eyeballs towards the position of the at least one instrument, and the corresponding pluralities of tracking parameters fetched for the uncalibrated gaze vectors of the third subset; and estimating calibrated gaze vectors of the user's eyes corresponding to yet another next time instant, based on a plurality of tracking parameters determined from yet another next image captured at the yet another next time instant, by utilising the generated mapping.

Optionally, the method further comprises:

processing images captured by at least one real-world-facing camera to generate a depth image of the real-world environment, wherein the at least one real-world-facing camera is implemented in a vehicle;

reprojecting the depth image of the real-world environment from a perspective of the at least one real-world facing camera to a perspective of a position of a given eye of the user; and determining a focusing distance of the user's eyes for the uncalibrated gaze vectors of the first subset, by utilising the reprojected depth image, wherein the focusing distance of the user's eyes correspond to a forward axis of vision specific to the user.

DETAILED DESCRIPTION OF THE DRAWINGS

Referring to FIG. 1, illustrated is a block diagram of an architecture of a system 100 incorporating implicit gaze and focus distance calibration, in accordance with an embodiment of the present disclosure. With reference to FIG. 1, the system 100 comprises at least one tracking camera (for example, depicted as a tracking camera 102) and at least one processor (for example, depicted as a processor 104). Optionally, the system 100 further comprises at least one real-world-facing camera (for example, depicted as a real-world-facing camera 106). The processor 104 is communicably coupled to the tracking camera 102 and optionally, to the real-world-facing camera 106. The processor 104 is configured to perform various operations, as described earlier with respect to the aforementioned first aspect.

It may be understood by a person skilled in the art that FIG. 1 includes a simplified architecture of the system 100, for sake of clarity, which should not unduly limit the scope of the claims herein. It is to be understood that the specific implementation of the system 100 is provided as an example and is not to be construed as limiting it to specific numbers or types of tracking cameras, processors, and real-world-facing cameras. The person skilled in the art will recognize many variations, alternatives, and modifications of embodiments of the present disclosure.

Figure 2:
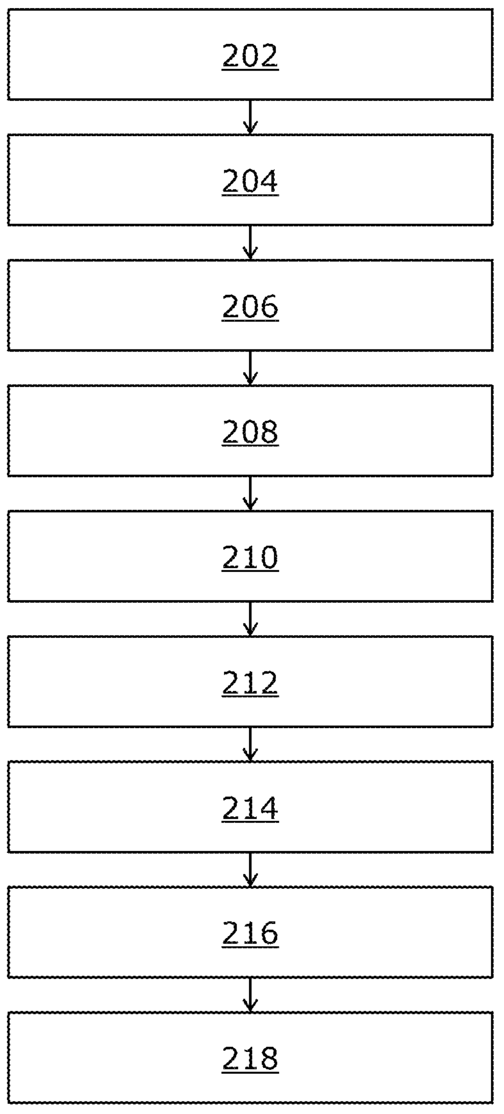
FIG. 2 illustrates steps of a method incorporating implicit gaze and focus distance calibration, in accordance with an embodiment of the present disclosure.

Referring to FIG. 2, illustrated are steps of a method incorporating implicit gaze and focus distance calibration, in accordance with an embodiment of the present disclosure. With reference to FIG. 2, at step 202, a plurality of images of a user's face is captured at a plurality of time instants, using at least one tracking camera. At step 204, a given image captured at a given time instant is processed to determine a plurality of tracking parameters comprising: a pose of the user's head, positions of eyeballs of the user's eyes, and at least one of: relative positions of irises of the user's eyes with respect to boundaries of the eyeballs, relative positions of irises of the user's eyes with respect to corners of the user's eyes, shapes of the user's eyes. At step 206, uncalibrated gaze vectors of the user's eyes corresponding to the given time instant are estimated, based on the plurality of tracking parameters determined from the given image. At step 208, a set of uncalibrated gaze vectors of the user's eyes corresponding to the plurality of time instants is generated, by performing said processing and said estimation for each of the plurality of images. At step 210, the uncalibrated gaze vectors of the set are at least temporarily stored along with corresponding time instants and corresponding pluralities of tracking parameters. At step 212, a first subset of uncalibrated gaze vectors is selected from amongst the set of uncalibrated gaze vectors whose direction matches with a predefined forward axis of vision. At step 214, corresponding pluralities of tracking parameters are fetched for the uncalibrated gaze vectors of the first subset. At step 216, a maximum distance between the irises of the user's eyes is determined, based on the corresponding pluralities of tracking parameters fetched for the uncalibrated gaze vectors of the first subset. At step 218, the maximum distance is considered as an interpupillary distance of the user for focusing distances greater than a predefined threshold distance.

The aforementioned steps are only illustrative and other alternatives can also be provided where one or more steps are added, one or more steps are removed, or one or more steps are provided in a different sequence without departing from the scope of the claims herein.

Figure 3:
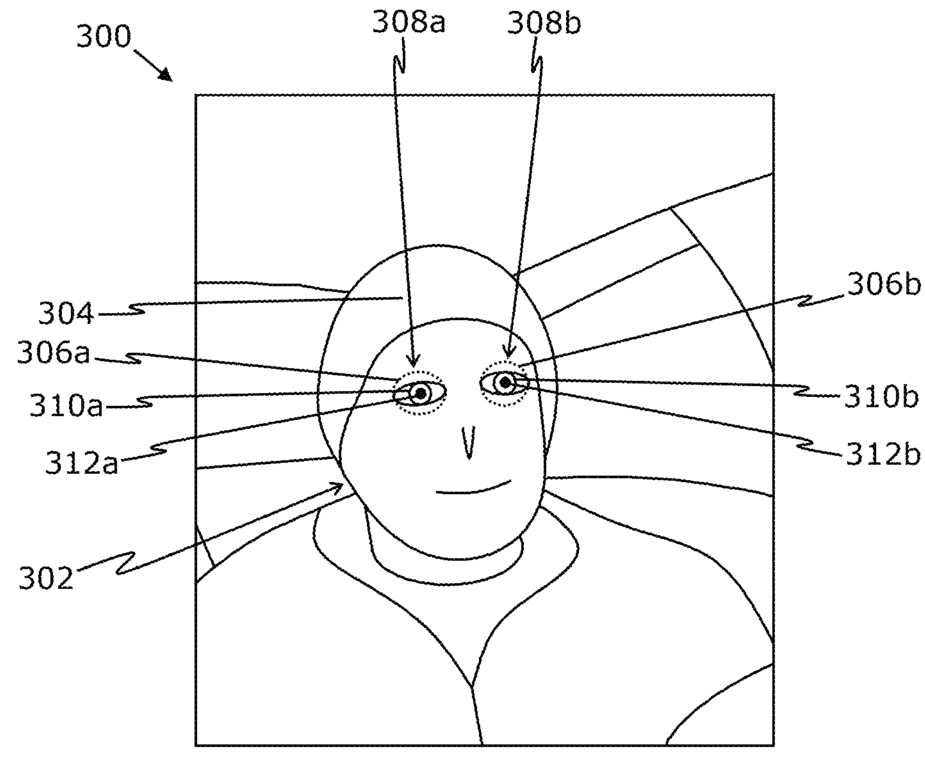
FIG. 3 illustrates an exemplary image of a user's face at a given time instant, in accordance with an embodiment of the present disclosure.

Referring to FIG. 3, illustrated is an exemplary image 300 of a user's face 302 at a given time instant, in accordance with an embodiment of the present disclosure. With reference to FIG. 3, the image 300 is captured using at least one tracking camera (not shown) arranged inside an enclosed space (for example, such as a cabin of a vehicle). The at least one tracking camera is understood to be arranged on a dashboard of the vehicle to face the user's face 302. The image 300 represents the user's face 302 and the user's head 304. The image 300 also represents eyeballs 306*a* and 306*b* (depicted using dotted circles) of the user's eyes 308*a* and 308*b*, irises 310*a* and 310*b* of the user's eyes 308*a* and 308*b*, and pupils 312*a* and 312*b* of the user's eyes 308*a* and 308*b*, respectively.

Figure 4A:
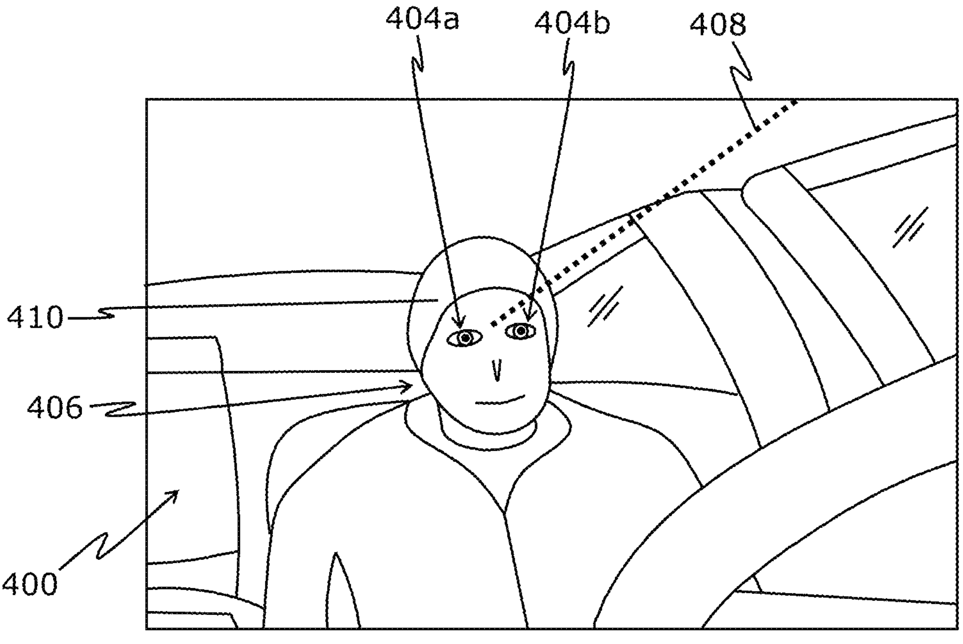
Figure 4B:
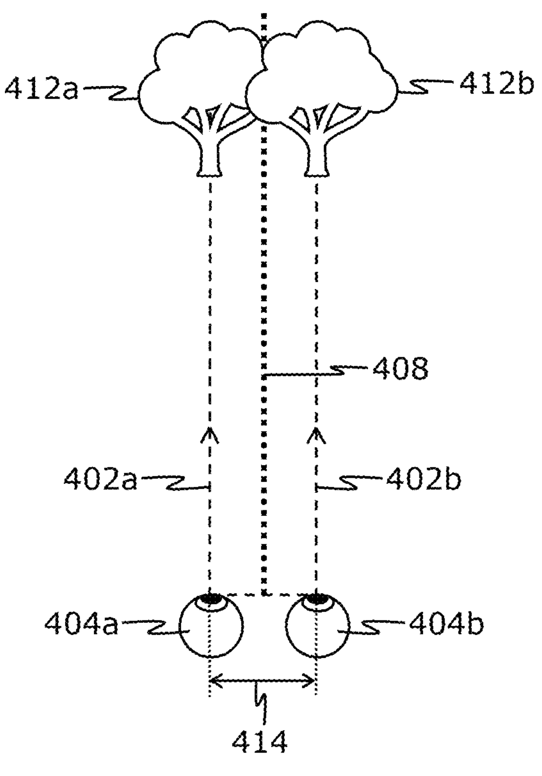
Figure 4C:
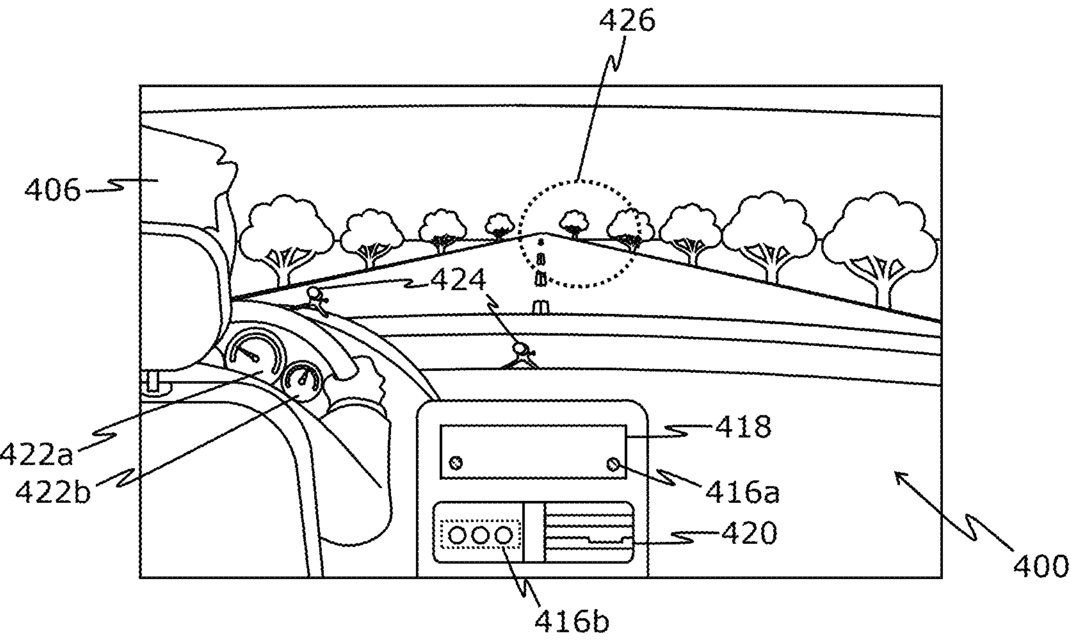
FIG. 4C illustrates locations of different exemplary elements within the enclosed space corresponding to different uncalibrated gaze vectors of the user's eyes, in accordance with an embodiment of the present disclosure.

Referring to FIGS. 4A, 4B, and 4C, FIG. 4A illustrates an enclosed space 400 where a system incorporating implicit gaze and focus distance calibration is employed, FIG. 4B illustrates uncalibrated gaze vectors 402*a* and 402*b* (depicted as dashed lines with arrows) of user's eyes 404*a* and 404*b*, while FIG. 4C illustrates locations of different exemplary elements within the enclosed space 400 corresponding to different uncalibrated gaze vectors of the user's eyes 404*a* and 404*b*, in accordance with an embodiment of the present disclosure.

With reference to FIGS. 4A and 4C, the enclosed space 400 is implemented as a cabin of a vehicle (for example, such as a car). A user 406 is shown to be present (i.e., seated) inside the vehicle, and is driving the vehicle. For sake of clarity and tidiness, some elements are shown only in FIG. 4A, while other elements are shown only in FIG. 4B. With reference to FIGS. 4A and 4B, a predefined forward axis 408 of vision is shown as a dotted line, wherein the predefined forward axis 408 of vision is an imaginary line extending from an average position of the user's eyes 404*a* and 404*b* (that corresponds to a viewing position of the user's head 410) in a direction that aligns with a line of sight of the user 406 when the user 406 is looking straight ahead within a field of view of the user 406 (while the user is driving the vehicle). Different users would have different forward axes of vision due to various factors, for example, such as different heights, different body postures, and other anatomical differences. It will be appreciated that a predefined forward axis of vision could be predefined based on a use case. As shown, in some cases, when the user 406 is present inside the vehicle and is driving the vehicle, the predefined forward axis 408 of vision is be predefined to be parallel to a longitudinal axis of the vehicle.

With reference to FIG. 4B, the user 406 gazes at a real-world object (for example, depicted as a tree) that lies at a near-infinite distance from the user's eyes 404*a* and 404*b* in a manner that the uncalibrated gaze vector 402*a* corresponds to a first eye 404*a* of the user 406 and the uncalibrated gaze vector 402*b* corresponds to a second eye 404*b* of the user 406. Due to binocular disparity, from a perspective of the first eye 404*a*, the tree is visible as a real-world object 412*a*, whereas from a perspective of the second eye 404*b*, the same tree is visible as a real-world object 412*b*. A distance between the first eye 404*a* and the second eye 404*b* is shown as an interpupillary distance (IPD) 414.

With reference to FIG. 4C, there are shown locations of input options 416*a* and 416*b* to be selected by the user 406, for example, at different time instants. It will be appreciated that a given input option could, for example, be selected at a given input device arranged inside the enclosed space 400. As an example, when a given input device is a display 418, the input option 416*a* could be a virtual option (such as a navigation page) being displayed at the display 418. As another example, when a given input device is an air conditioner control panel 420, the input option 416*b* could be a physical button at the air conditioner control panel 420. Furthermore, there are also shown location of instruments 422*a* (for example, depicted as a speedometer of the vehicle) and 422*b* (for example, depicted as a fuel indicator of the vehicle) being used in the enclosed space 400. There is also shown a location of at least one tracking camera (for example, depicted as two tracking cameras 424, only for sake of simplicity) arranged inside the enclosed space 400, wherein the tracking cameras 424 are arranged on a dashboard of the vehicle (at different locations) to face the user's face. Moreover, while driving the vehicle, the uncalibrated gaze vectors 402*a* and 402*b* (as shown in FIG. 4B) correspond to a region of interest 426 lying approximately at a central part within the field of view of the user 406. As an example, said region of interest 426 is shown to comprise a portion of a road on which the vehicle is being driven, at least a portion of at least one tree, and a portion of the sky.

Figure 5:
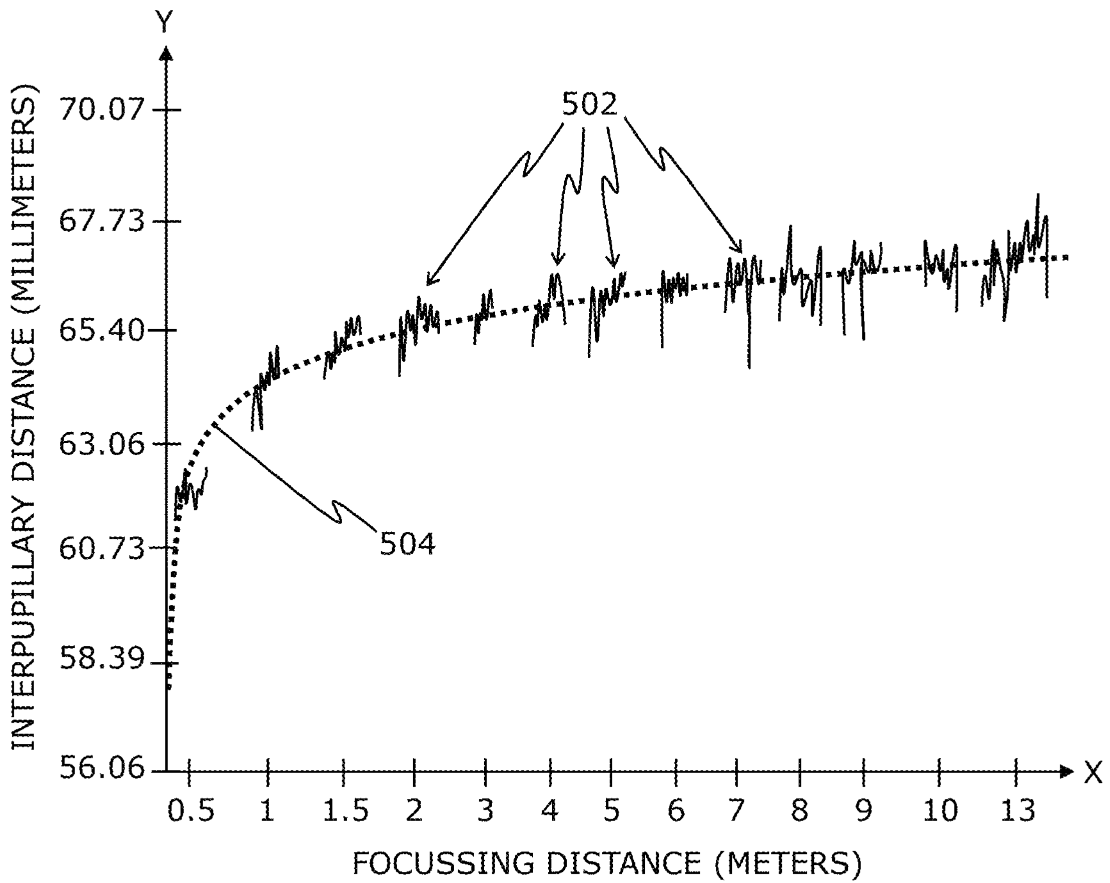
FIG. 5 illustrates an exemplary graphical representation of a variation of a distance between irises of a user's eyes as a function of a focusing distance of the user's eyes, in accordance with an embodiment of the present disclosure.

Referring to FIG. 5, illustrated is an exemplary graphical representation of a variation of a distance between irises of user's eyes as a function of a focusing distance of the user's eyes, in accordance with an embodiment of the present disclosure. With reference to FIG. 5, a positive X-axis represents the focusing distance of the user's eyes (for example, in metres), and a positive Y-axis represents interpupillary distance of the user's eyes (for example, in millimetres). Herein, for different focusing distances, different variations 502 of the distance between the irises of the user's eyes is shown. A trend 504 (depicted using a dotted line curve) shows that greater the focusing distance of the user's eyes, greater is the interpupillary distance of the user's eyes. This is due to the fact that when the user focusses on a nearby object (namely, an object located at a distance less than a predefined threshold distance, for example, such as 10 metres), pupils of the user's eyes constricts, causing a slight decrease in the distance between the irises of the user's eyes, and also in the interpupillary distance. Conversely, when the user focusses on a far object (namely, an object located at a distance greater than the predefined threshold distance), pupils of the user's eyes dilate to allow additional light to enter the user's eyes. Such a dilation of the pupils results in a slight increase in the distance between the irises of the user's eyes, and also in the interpupillary distance. When said far object is assumed to be located at infinity or near-infinity, there would be a maximum distance between the irises of the user's eyes. It will be appreciated that said variations 502 are collected by way of conducting an experiment, and are specific to a particular user (namely, user-specific), and thus may vary differently for different users.

FIGS. 3, 4A, 4B, 4C, and 5 are merely examples, which should not unduly limit the scope of the claims herein. A person skilled in the art will recognize many variations, alternatives, and modifications of embodiments of the present disclosure.

The invention claimed is:

1. A system comprising:

at least one tracking camera; and at least one processor configured to:

capture a plurality of images of a user's face at a plurality of time instants, using the at least one tracking camera;

process a given image captured at a given time instant, to determine a plurality of tracking parameters comprising: a pose of the user's head, positions of eyeballs of the user's eyes, and at least one of: relative positions of irises of the user's eyes with respect to boundaries of the eyeballs, relative positions of irises of the user's eyes with respect to corners of the user's eyes, and shapes of the user's eyes;

estimate uncalibrated gaze vectors of the user's eyes corresponding to the given time instant, based on the plurality of tracking parameters determined from the given image;

generate a set of uncalibrated gaze vectors of the user's eyes corresponding to the plurality of time instants, by performing said processing and said estimation for each of the plurality of images;

store at least temporarily the uncalibrated gaze vectors of the set along with corresponding time instants and corresponding pluralities of tracking parameters;

select, from amongst the set of uncalibrated gaze vectors, a first subset of uncalibrated gaze vectors whose direction matches with a predefined forward axis of vision;

for the uncalibrated gaze vectors of the first subset, fetch corresponding pluralities of tracking parameters;

determine a maximum distance between the irises of the user's eyes, based on the corresponding pluralities of tracking parameters fetched for the uncalibrated gaze vectors of the first subset; and consider the maximum distance as an interpupillary distance of the user for focusing distances greater than a predefined threshold distance.

2. The system of claim 1, wherein the at least one processor is configured to:

generate a mapping between a forward axis of vision specific to the user and the corresponding pluralities of tracking parameters fetched for the uncalibrated gaze vectors of the first subset; and estimate calibrated gaze vectors of the user's eyes corresponding to a next time instant, based on a plurality of tracking parameters determined from a next image captured at the next time instant, by utilising the generated mapping.

3. The system of claim 1, wherein the at least one processor is configured to:

detect an input event pertaining to a selection of an input option by the user;

when the input event is detected, determine a position of the input option selected by the user and a time instant at which the input option was selected by the user;

select, from amongst the set of uncalibrated gaze vectors, a second subset of uncalibrated gaze vectors whose corresponding time instants lie within a predefined time period from the time instant at which the input option was selected by the user, and whose direction matches with viewing directions pointing from the positions of the eyeballs towards the position of the input option;

for the uncalibrated gaze vectors of the second subset, fetch corresponding pluralities of tracking parameters; and determine a focusing distance of the user's eyes corresponding to when the user is looking at the input option, based on a distance between the position of the input option and the positions of eyeballs of the user's eyes in the corresponding pluralities of tracking parameters fetched for the uncalibrated gaze vectors of the second subset.

4. The system of claim 3, wherein the at least one processor is configured to:

determine a distance between the irises of the user's eyes, based on the corresponding pluralities of tracking parameters fetched for the uncalibrated gaze vectors of the second subset; and consider the distance as an interpupillary distance of the user for the focusing distance of the user's eyes corresponding to when the user is looking at the input option.

5. The system of claim 3, wherein the at least one processor is configured to:

generate a mapping between the viewing directions pointing from the positions of the eyeballs towards the position of the input option, and the corresponding pluralities of tracking parameters fetched for the uncalibrated gaze vectors of the second subset; and estimate calibrated gaze vectors of the user's eyes corresponding to another next time instant, based on a plurality of tracking parameters determined from another next image captured at the another next time instant, by utilising the generated mapping.

6. The system of claim 1, wherein the system is implemented in an enclosed space in which at least one instrument is being used, and wherein the at least one processor is configured to:

select, from amongst the set of uncalibrated gaze vectors, a third subset of uncalibrated gaze vectors whose direction matches with viewing directions pointing from the positions of the eyeballs towards a position of the at least one instrument;

for the uncalibrated gaze vectors of the third subset, fetch corresponding pluralities of tracking parameters; and determine a focusing distance of the user's eyes corresponding to when the user is looking at the at least one instrument, based on a distance between the position of the at least one instrument and the positions of eyeballs of the user's eyes in the corresponding pluralities of tracking parameters fetched for the uncalibrated gaze vectors of the third subset.

7. The system of claim 6, wherein the at least one processor is configured to:

determine a distance between the irises of the user's eyes, based on the corresponding pluralities of tracking parameters fetched for the uncalibrated gaze vectors of the third subset; and consider the distance as an interpupillary distance of the user for the focusing distance of the user's eyes corresponding to when the user is looking at the at least one instrument.

8. The system of claim 6, wherein the at least one processor is configured to:

generate a mapping between the viewing directions pointing from the positions of the eyeballs towards the position of the at least one instrument, and the corresponding pluralities of tracking parameters fetched for the uncalibrated gaze vectors of the third subset; and estimate calibrated gaze vectors of the user's eyes corresponding to yet another next time instant, based on a plurality of tracking parameters determined from yet another next image captured at the yet another next time instant, by utilising the generated mapping.

9. The system of claim 1, wherein the system is implemented in a vehicle, the system further comprising at least one real-world-facing camera, wherein the at least one processor is configured to:

process images captured by the at least one real-world-facing camera, to generate a depth image of the real-world environment;

reproject the depth image of the real-world environment from a perspective of the at least one real-world facing camera to a perspective of a position of a given eye of the user; and for the uncalibrated gaze vectors of the first subset, determine a focusing distance of the user's eyes corresponding to a forward axis of vision specific to the user, by utilising the reprojected depth image.

10. A method comprising:

capturing a plurality of images of a user's face at a plurality of time instants, using at least one tracking camera;

processing a given image captured at a given time instant, to determine a plurality of tracking parameters comprising: a pose of the user's head, positions of eyeballs of the user's eyes, and at least one of: relative positions of irises of the user's eyes with respect to boundaries of the eyeballs, relative positions of irises of the user's eyes with respect to corners of the user's eyes, and shapes of the user's eyes;

estimating uncalibrated gaze vectors of the user's eyes corresponding to the given time instant, based on the plurality of tracking parameters determined from the given image;

generating a set of uncalibrated gaze vectors of the user's eyes corresponding to the plurality of time instants, by performing said processing and said estimation for each of the plurality of images;

storing at least temporarily the uncalibrated gaze vectors of the set along with corresponding time instants and corresponding pluralities of tracking parameters;

selecting, a first subset of uncalibrated gaze vectors from amongst the set of uncalibrated gaze vectors whose direction matches with a predefined forward axis of vision;

fetching corresponding pluralities of tracking parameters for the uncalibrated gaze vectors of the first subset;

determining a maximum distance between the irises of the user's eyes, based on the corresponding pluralities of tracking parameters fetched for the uncalibrated gaze vectors of the first subset; and considering the maximum distance as an interpupillary distance of the user for focusing distances greater than a predefined threshold distance.

11. The method of claim 10, further comprising:

generating a mapping between a forward axis of vision specific to the user and the corresponding pluralities of tracking parameters fetched for the uncalibrated gaze vectors of the first subset; and estimating calibrated gaze vectors of the user's eyes corresponding to a next time instant, based on a plurality of tracking parameters determined from a next image captured at the next time instant, by utilising the generated mapping.

12. The method of claim 10, further comprising:

detecting an input event pertaining to a selection of an input option by the user;

when the input event is detected, determining a position of the input option selected by the user and a time instant at which the input option was selected by the user;

selecting, from amongst the set of uncalibrated gaze vectors, a second subset of uncalibrated gaze vectors whose corresponding time instants lie within a predefined time period from the time instant at which the input option was selected by the user, and whose direction matches with viewing directions pointing from the positions of the eyeballs towards the position of the input option;

fetching corresponding pluralities of tracking parameters for the uncalibrated gaze vectors of the second subset; and determining a focusing distance of the user's eyes corresponding to when the user is looking at the input option, based on a distance between the position of the input option and the positions of eyeballs of the user's eyes in the corresponding pluralities of tracking parameters fetched for the uncalibrated gaze vectors of the second subset.

13. The method of claim 12, further comprising:

determining a distance between the irises of the user's eyes, based on the corresponding pluralities of tracking parameters fetched for the uncalibrated gaze vectors of the second subset; and considering the distance as an interpupillary distance of the user for the focusing distance of the user's eyes corresponding to when the user is looking at the input option.

14. The method of claim 12, further comprising:

generating a mapping between the viewing directions pointing from the positions of the eyeballs towards the position of the input option, and the corresponding pluralities of tracking parameters fetched for the uncalibrated gaze vectors of the second subset; and estimating calibrated gaze vectors of the user's eyes corresponding to another next time instant, based on a plurality of tracking parameters determined from another next image captured at the another next time instant, by utilising the generated mapping.

15. The method of claim 10, further comprising:

selecting, from amongst the set of uncalibrated gaze vectors, a third subset of uncalibrated gaze vectors whose direction matches with viewing directions pointing from the positions of the eyeballs towards a position of at least one instrument, wherein the at least one instrument is being used in an enclosed space;

fetching corresponding pluralities of tracking parameters for the uncalibrated gaze vectors of the third subset; and determining a focusing distance of the user's eyes corresponding to when the user is looking at the at least one instrument, based on a distance between the position of the at least one instrument and the positions of eyeballs of the user's eyes in the corresponding pluralities of tracking parameters fetched for the uncalibrated gaze vectors of the third subset.

16. The method of claim 15, further comprising:

determining a distance between the irises of the user's eyes, based on the corresponding pluralities of tracking parameters fetched for the uncalibrated gaze vectors of the third subset; and considering the distance as an interpupillary distance of the user for the focusing distance of the user's eyes corresponding to when the user is looking at the at least one instrument.

17. The method of claim 15, further comprising:

generating a mapping between the viewing directions pointing from the positions of the eyeballs towards the position of the at least one instrument, and the corresponding pluralities of tracking parameters fetched for the uncalibrated gaze vectors of the third subset; and estimating calibrated gaze vectors of the user's eyes corresponding to yet another next time instant, based on a plurality of tracking parameters determined from yet another next image captured at the yet another next time instant, by utilising the generated mapping.

18. The method of claim 10, further comprising:

processing images captured by at least one real-world-facing camera to generate a depth image of the real-world environment, wherein the at least one real-world-facing camera is implemented in a vehicle;

reprojecting the depth image of the real-world environment from a perspective of the at least one real-world facing camera to a perspective of a position of a given eye of the user; and determining a focusing distance of the user's eyes for the uncalibrated gaze vectors of the first subset, by utilising the reprojected depth image, wherein the focusing distance of the user's eyes correspond to a forward axis of vision specific to the user.

* * * * *